(12) United States Patent
Schneider

(10) Patent No.: US 6,410,742 B1
(45) Date of Patent: Jun. 25, 2002

(54) POLYMORPHS OF TELMISARTAN

(75) Inventor: Heinrich Schneider, deceased, late of Ingelheim (DE), by Margarete Schneider, Legal Representative

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/992,621

(22) Filed: Nov. 16, 2001

Related U.S. Application Data

(62) Division of application No. 09/480,211, filed on Jan. 10, 2000, now Pat. No. 6,358,986.
(60) Provisional application No. 60/128,311, filed on Apr. 8, 1999.

(30) Foreign Application Priority Data

Jan. 19, 1999 (DE) .......................................... 199 01 921

(51) Int. Cl.⁷ ............................................. C07D 403/04
(52) U.S. Cl. .................................................... 548/305.4
(58) Field of Search ....................................... 548/305.4

(56) References Cited

FOREIGN PATENT DOCUMENTS

EP        0 502 314 B1       9/1992

OTHER PUBLICATIONS

Ries, U. J., et al; "6–Substituted Benzimidazoles as New Nonpeptide Angiotensin II Receptor Antagonists: Synthesis, Biological Activity, and Structure–Activity Relationships"; J. Med. Chem. 1993, 36, 4040–4051.

*Primary Examiner*—Laura L. Stockton
(74) *Attorney, Agent, or Firm*—Robert P. Raymond; Alan R. Stempel; Mary-Ellen M. Devlin

(57) ABSTRACT

The invention relates to polymorphs of 4'-[2-n-propyl-4-methyl-6-(1-methylbenzimid azol-2-yl)benzimidazol-1-ylmethyl]biphenyl-2-carboxylic acid (INN: telmisartan), particularly polymorphic form B, mixtures of the polymorphs, processes for preparing telmisartan containing form B and the use thereof for preparing a pharmaceutical composition.

7 Claims, 1 Drawing Sheet

POLYMORPHS OF TELMISARTAN

Related Applications

This is a division of Ser. No. 09/480,211, filed Jan. 10, 2000, now U.S. Pat. No. 6,358,986 which claims benefit of prior provisional application Ser. No. 60/128,311, filed on April 8, 1999.

Background of the Invention

(1) Field of the Invention

The invention relates to polymorphs of 4'-[2-n-propyl-4-methyl-6-(1-methylbenzimid azol-2-yl)benzimidazol- 1-ylmethyl]biphenyl-2-carboxylic acid (INN: telmisartan), particularly the polymorphic form B, mixtures of the polymorphs, processes for preparing telmisartan containing form B and the use thereof for preparing a pharmaceutical composition.

(2) Description of the Related Art

The compound telmisartan is known from European Patent EP 502 314 B1 and has the following chemical structure:

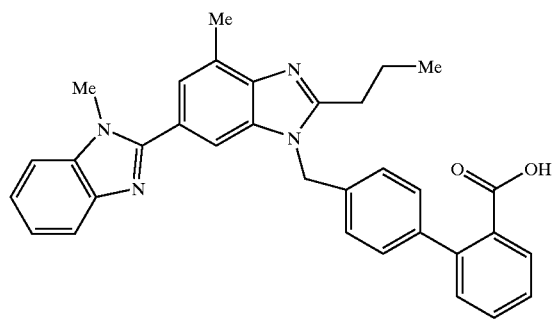

(I)

Telmisartan and the physiologically acceptable salts thereof have valuable pharmacological properties. Telmisartan is an angiotensin antagonist, particularly an angiotensin-II-antagonist which by virtue of its pharmacological properties may be used for example to treat hypertension and cardiac insufficiency, to treat ischaemic peripheral circulatory disorders, myocardial ischaemia (angina), to prevent the progression of cardiac insufficiency after myocardial infarct, to treat diabetic neuropathy, glaucoma, gastrointestinal diseases and bladder diseases. Other possible therapeutic applications can be found in EP 502314 B1, the contents of which are hereby referred to.

In the course of the synthesis of telmisartan, the final step of the synthesis comprises saponifying the tert.butyl ester (II) according to Diagram 1.

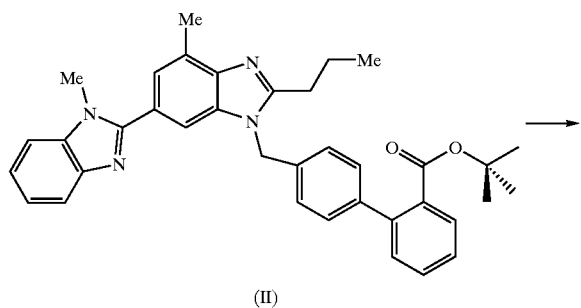

(II)

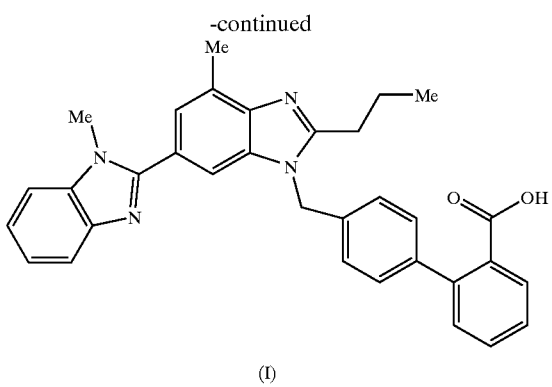

(I)

Diagram 1:

The corresponding experimental procedure which may be carried out on a laboratory scale can be found in EP 502314 B1. Surprisingly, however, it proved to be problematic to transfer the method of synthesis already known to a large-scale industrial manufacturing process. The telmisartan synthesised on an industrial scale according to Diagram 1 is obtained after working up in the form of a product which has to be subjected to a further crystallisation step to complete the purification. In this obligatory crystallisation step the morphology of the end product which crystallises out leads to unforeseen problems.

The product which is precipitated as a solid in the form of long needles is difficult to filter, wash and isolate, is further characterised by a very long drying time on account of the presence of solvent and forms large, very hard fragments during the drying process. Grinding these fragments produces a dry powder which exhibits a strong tendency to electrostatic charging and is virtually impossible to pour.

The disadvantageous properties of a product as described above have always proved to be a serious obstacle to the large-scale manufacture of a compound, as reproducible manufacture of large amounts of the compound in highly pure form is only possible with considerable difficulty or with high additional technical costs.

The aim of the present invention is therefore to prepare telmisartan in a form which permits the large-scale synthesis, working up, purification and isolation of telmisartan in which the above disadvantages are overcome.

DESCRIPTION OF THE INVENTION

Surprisingly, it has been found that telmisartan may occur as a solid in different crystalline modifications. Depending on the nature of the crystallisation process it may be converted into two different polymorphic forms A and B.

Polymorph A is a form of telmisartan which is obtainable according to the prior art, and which gives rise to the abovementioned problems in large-scale manufacture or purification, isolation and drying of the product.

The polymorphic form B of telmisartan which was surprisingly found, however, shows virtually no tendency to electrostatic charging, is easy to suction filter, centrifuge, wash and dry and is free-flowing even without being ground up.

The following procedure is used according to the invention to prepare the polymorphic form B of telmisartan.

Crude telmisartan product (crystallised for example from dimethylformamide, dimethylacetamide or the like) is taken up, in a suitably sized stirring apparatus, optionally with 1–5 wt.-%, preferably with 3 wt.-% of activated charcoal in a mixture of solvents consisting of water, formic acid and a suitable organic solvent and then dissolved at elevated temperature, preferably at a temperature of from 50–90° C., most preferably at 60–80° C.

According to the invention it is essential to use the solvent mixture of formic acid and water with an organic solvent which must satisfy the following criteria according to the invention. It must be capable of forming a solution with the mixture of formic acid and water. It must be largely chemically inert relative to the mixture of formic acid and water and it must be capable of being separated from the mixture of formic acid and water by distillation. Organic carboxylic acid esters, ketones or ethers may be used. Acetone, methylethylketone, methyl acetate, ethyl acetate, ethyl formfate, ethyleneglycol dimethylether or tetrahydrofuran may be mentioned by way of example. Acetone, methylethylketone, methyl acetate, ethyl acetate and THF are preferred according to the invention, while ethyl acetate is particularly preferred. According to the invention, the mixture of solvents should be made up of 0.3–0.7 l of water, 10–15 mol of formic acid and 0.3–0.9 l of the organic solvent per mol of telmisartan. A ratio of 0.4–0.6 l of water, 11–13 mol of formic acid and 0.4–0.7 l of the organic solvent based on 1 mol of telmisartan is preferred. A ratio of about 0.5 l of water, about 11.5–12 mol of formic acid and about 0.5 l of the organic solvent based on 1 mol of telmisartan is particularly preferred.

According to the invention, after the abovementioned heating, the solution obtained is filtered and washed with a mixture of the abovementioned organic solvent and formic acid. The washing solution may contain 0.3–1.0 mol, preferably 0.4–0.6 mol, most preferably about 0.5 mol of formic acid per mol of telmisartan. The quantity of washing solution will naturally depend on the quantity of dissolved telmisartan. According to the invention, 0.1–0.4, preferably 0.15–0.3, most preferably 0.2 l of the organic solvent are used to each mol of telmisartan.

After the filter residue has been washed with the washing solution described above, the organic solvent is distilled off as much as possible whilst water is added simultaneously. The temperature is kept in the range from 60–100° C., preferably from 70–100° C. The total quantity of water added corresponds substantially to the total amount of solvent distilled off. Almost total distillation of the organic solvent is desirable according to the invention. Accordingly, the distillation is continued until water is also distilled off, partly azeotropically. The organic solvent distilled off may be used again in subsequent reactions, if necessary after removal of the aqueous phase.

In order to precipitate the telmisartan-polymorphic B it is then cooled to a temperature in the range from 15–60° C., preferably to 20–30° C., and precipitated with a base. The quantity of base to be used depends on the amount of formic acid used. Preferably, 0–2 mol less base is added than there is formic acid present. Most preferably, 0.3–1.5 mol less base is added than there is formic acid present. It is most particularly preferred to add 0.5–1 mol less base than there is formic acid present. Suitable bases might be either aqueous solutions of potassium hydroxide, sodium hydroxide, lithium hydroxide or ammonia. It is also possible to use suitable organic bases such as triethylamine, diisopropylethylamine or DBU (diazabicycloundecene). Particularly preferred bases are the abovementioned aqueous solutions of the potassium hydroxide, sodium hydroxide, lithium hydroxide or ammonia, the aqueous solutions of ammonia being particularly important.

The product precipitated is centrifuged, washed with water and normally dried in vacuo at 120–125° C.

A sample taken directly after centrifuging and dried in a thin layer in a circulating air drier in the laboratory typically shows a content of 95–99% of crystalline form B. After centrifugation, the product begins to change partially into form A, depending on the temperature, pH, retention time, and water content, towards the end of the drying. Therefore, in working mixtures, ratios of form A to form B of at best about 10:90 are obtained after drying, but ratios of 60:40 may also be obtained.

However, even a content of form B as low as this guarantees that the product will have the positive qualities required for large-scale production (e.g. a low tendency to electrostatic charging, a low tendency to clumping, free-flowing characteristics etc.). What is essential to the invention in the crystallisation process mentioned above is that initially only form B is produced, with its characteristic macroscopic crystalline form. This macroscopic crystalline form is largely retained under the drying conditions, in spite of partial microscopic rearrangement into form A.

Other highly advantageous aspects of the procedure according to the invention are the high space/time yield of the present process and the high yield of pure telmisartan product, which can be isolated in virtually quantitative amounts.

The telmisartan of form A which can be obtained by the manufacturing process known from the prior art differs from the telmisartan obtainable according to the invention, which is characterised in that it contains some polymorphic form B, in the advantageous qualities of the product already mentioned hereinbefore. Other distinguishing features will be described hereinafter.

Telmisartan of form A crystallises as long, fine or thin needles which cling together in a felt-like manner. The crystal modification of telmisartan of form B produces very compact cubic to spherical crystals which trickle like sand or silica gel.

BRIEF DESCRIPTION OF THE DRAWING

The two polymorph forms A and B of telmisartan differ considerably in their melting point. Form B melts at 183+/−2° C. (determined by DSC), form A at 269+/−2° C. (determined by DSC). After melting, the lower-melting form B of telmisartan crystallises out again as form A. This results, for example, in the endothermic maximum at 183+/−2° C. determined by DSC being followed by a characteristic exothermic maximum which reflects the crystallisation of the melt of form B into the high-melting form A. The DSC diagrams (DSC=Differential Scanning Calorimetry) obtained with a Mettler DSC-20, TA8000 system are shown in FIG. 1.

The polymorphs A and B also differ in their IR spectrum. On the basis of this difference, the IR spectroscopy may optionally be used for quantitative determination of the ratio of the two crystal modifications in the end product after drying. Pure polymorph A has a characteristic band at 815cm$^{-1}$ in the IR spectrum. In polymorph B this oscillation is shifted to 830cm$^{-1}$. Since these two characteristic bands of polymorphs A and B are sufficiently far apart, they are particularly suitable for the abovementioned quantitative determination of the ratio of the two crystal modifications.

Figure 1:
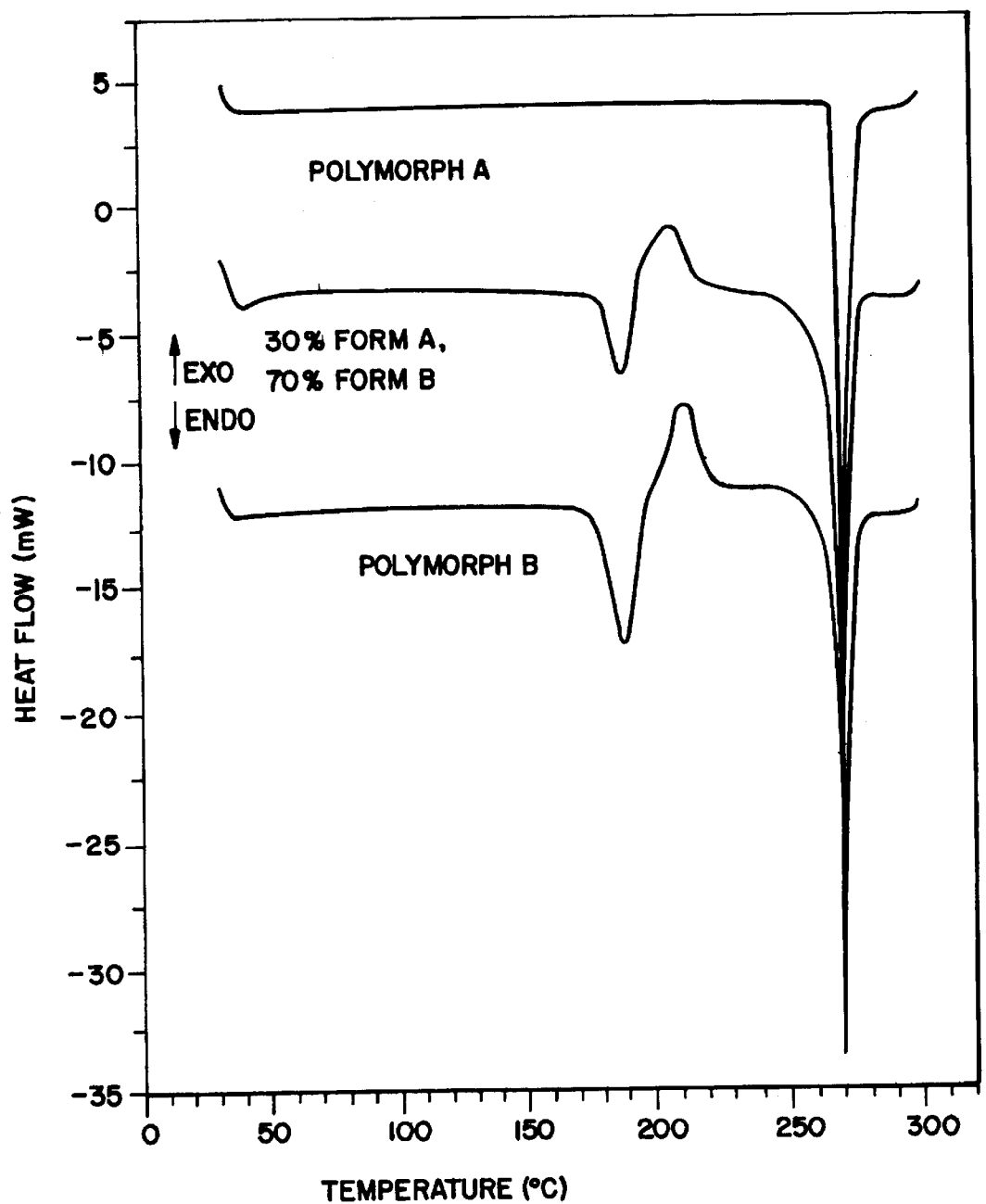

The IR-spectroscopic characterisation of the two polymorphic forms A and B was carried out using the Nicolet FTIR Spectrometer Magna—IR 550 in KBr (2.5 µmol per 300 mg KBr; Nicolet software package OMNIC, version 1.20).

The Examples which follow serve to illustrate purification and crystallisation processes carried out by way of example in order to prepare the polymorphic form B of telmisartan. They should be regarded purely as possible procedures described by way of example, without restricting the invention to their contents.

EXAMPLE 1

205.6 kg of recrystallised telmisartan (recrystallised from dimethylformamide or dimethylacetamide), 6.2 kg of activated charcoal, 205.6 l of water, 211.6 kg of formic acid (99–100%) and 205.6 l of ethyl acetate are placed in a 1200 l stirring apparatus. The mixture is stirred for about 1 h at 70–80° C. and then filtered into another 1200 l stirring apparatus and washed with a mixture of 82.2 l of ethyl acetate and 9.2 kg of formic acid (99–100%). About 308 l of solvent are distilled off at 80–100° C. whilst simultaneously 308 l of water are added. The mixture is then cooled to 20–30° C. and precipitated by the metered addition of 313 kg of 25% ammonia solution. The product precipitated is centrifuged, washed with water and dried at 120–125° C.

Yield: 200 kg telmisartan (97.3% of theory).

EXAMPLE 2

185 kg of recrystallised telmisartan (recrystallised from dimethylformamide or dimethylacetamide), 5.6 kg of activated charcoal, 185 l of water, 190.4 kg of formic acid (99–100%) and 185 l of tetrahydrofuran are placed in a 1200 l stirring apparatus. The mixture is stirred for about 1 h at 60–70° C. and then filtered into another 1200 l stirring apparatus and washed with a mixture of 74 l of tetrahydrofuran and 8.3 kg of formic acid (99–100%). About 278 l of solvent are distilled off at 70–100IC whilst simultaneously 278 l of water are added. The mixture is then cooled to 20–30° C. and precipitated by the metered addition of 281.5 kg of 25% ammonia solution. The product precipitated is centrifuged, washed with water and dried at 120–125° C.

Yield: 180 kg telmisartan (97.3% of theory).

EXAMPLE 3

185 kg of recrystallised telmisartan (recrystallised from dimethylformamide or dimethylacetamide), 5.6 kg of activated charcoal, 185 l of water, 190.4 kg of formic acid (99–100%) and 185 l of methylethylketone are placed in a 1200 l stirring apparatus. The mixture is stirred for about 1 h at 60–70° C. and then filtered into another 1200 l stirring apparatus and washed with a mixture of 74 l of methylethylketone and 8.3 kg of formic acid (99–100%). About 278 l of solvent are distilled off at 80–1 00C whilst simultaneously 278 l of water are added. The mixture is then cooled to 20–30° C. and precipitated by the metered addition of 281.5 kg of 25% ammonia solution. The product precipitated is centrifuged, washed with water and dried at 120–125° C.

Yield: 178 kg of telmisartan (96.2% of theory).

COMPARISON EXAMPLE 150 kg of telmisartan (recrystallised from dimethylformamide or dimethylacetamide), 7.5 kg of activated charcoal, 750 l of ethanol and 30 kg of 25% aqueous ammonia solution are placed in a 1200 l stirring apparatus. The mixture is stirred for about 1 h and then filtered into another 1200 l stirring apparatus and washed with 150 l of ethanol. The mixture is heated to 70–80° C., 35 kg of glacial acetic acid are added and the mixture is stirred for a further 1.5–2 h at 75–80° C. The mixture is then cooled to 0–10IC and stirred for a further 2 h. The product precipitated is centrifuged, washed with 300 l of ethanol and with 300 l of water and dried at 70–90° C.

Yield: 135 kg of telmisartan (90% of theory) pure form A.

In the preparation process according to the invention, as a result of the partial conversion of the polymorphic form B into the polymorphic form A during the drying process, telmisartan occurs as a pure substance in a mixture of two polymorphic forms. However, this does not affect the properties of the pharmaceutical composition, as in the course of the manufacture of telmisartan tablets, for example, the mixture of the polymorphic forms A and B is dissolved in 0.1 N NaOH solution and converted by spray drying into a homogeneous and totally amorphous granulate which is then subjected to the other tablet making steps. For more detailed information on the use of the products according to the invention for preparing a pharmaceutical composition, cf. EP 502314 B1, the contents of which are hereby referred to.

What is claimed is:

1. A process for preparing telmisartan (the compound of formula I)

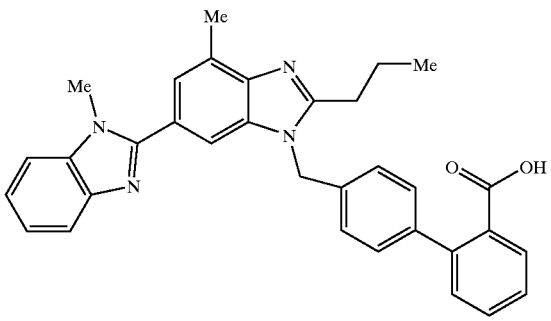

(I)

comprising a mixture of two polymorphic crystalline forms, wherein the first polymorphic crystalline form, designated form A, has an endothermic maximum at 269±2° C. which occurs during thermal analysis using DSC, and wherein the second polymorphic crystalline form, designated form B, has endothermic maxima at 183±2° C. and at 269±2° C. which occur during thermal analysis using DSC, which process comprises the following steps:

(a) dissolving telmisartan comprising form A but substantially no form B in a mixture of solvents consisting of water, formic acid and an organic solvent that is miscible therewith, (b) heating the solution created in the preceding step, (c) distilling the solution to remove the organic solvent, (d) precipitating the telmisartan comprising forms A and B out of the remaining solution by the addition of a base, and (e) removing the precipitated telmisartan comprising forms A and B from the solution.

2. The process of claim 1 wherein the ratio of form A to form B in the mixture produced by the process is in the range from 10:90 to 60:40.

3. The process according to claim 1 or 2, wherein an organic carboxylic acid ester, a ketone or an ether is used as the organic solvent.

4. The process according to claim 1 or 2, wherein acetone, methylethylketone, methyl acetate, ethyl acetate, ethyl formate, ethyleneglycol dimethylether or tetrahydrofuran is used as the organic solvent.

5. The process according to claim 1 or 2, wherein acetone, methylethylketone, methyl acetate, ethyl acetate or tetrahydrofuran is used as the organic solvent.

6. The process according to claim 1 or 2, wherein ethyl acetate is used as the organic solvent.

7. The process according to claim 1 or 2, wherein ammonia is used as the base.

* * * * *